United States Patent [19]

Strauss et al.

[11] Patent Number: 5,707,232
[45] Date of Patent: Jan. 13, 1998

[54] ORTHODONTIC BUCCAL APPLIANCE

[75] Inventors: Morris Strauss, Ramat Hasharon; Yigal Ringart, Givat Ela, both of Israel

[73] Assignee: Orthoject Ltd., Herzliya Pituach, Israel

[21] Appl. No.: 660,210

[22] Filed: Jun. 3, 1996

Related U.S. Application Data

[63] Continuation of Ser. No. 338,735, Nov. 9, 1994, abandoned.

[30] Foreign Application Priority Data

Nov. 18, 1993 [IL] Israel .................................. 107652

[51] Int. Cl.$^6$ ................................................ A61C 3/00
[52] U.S. Cl. ................................................ 433/17
[58] Field of Search ................................ 433/17, 5

[56] References Cited

U.S. PATENT DOCUMENTS

| 1,481,861 | 1/1924 | Eaton | 433/17 |
|---|---|---|---|
| 3,315,359 | 4/1967 | Moss | 433/17 |
| 3,335,496 | 8/1967 | Andrews et al. | 433/17 |
| 4,227,876 | 10/1980 | Fogel et al. | 433/11 |
| 4,781,582 | 11/1988 | Kesling | 433/17 |

FOREIGN PATENT DOCUMENTS 0 326 758  8/1989  European Pat. Off. .

*Primary Examiner*—John J. Wilson
*Attorney, Agent, or Firm*—Oliff & Berridge

[57] ABSTRACT

An orthodontic buccal tube device adapted to cooperate with an arch wire and comprising a base member for attachment to a tooth, and a body member which is fixed to the base member and which comprises a bore adapted to accommodate an end portion of the arch wire. The device comprises an auxiliary member fixed to or integral with either the base member or the body member and is adapted for cooperation with an end of the wire protruding from the bore to either limit the rearward movement of the wire, or exert a force bringing to the development of a moment in the wire, or both. The auxiliary member is also useful in forming an abutment in the direction of the buccal-mucosa, for ensuring appropriate distance between the buccal-mucosa and the end of the wire so as to avoid injuries to said mucosa.

19 Claims, 4 Drawing Sheets

5,707,232

ORTHODONTIC BUCCAL APPLIANCE

This is a Continuation of application Ser. No. 08/338,735 filed Nov. 9, 1994, now abandoned.

FIELD OF THE INVENTION

The present invention is in the field of orthodontic buccal tube appliances and more specifically it is directed to an improvement thereof for assisting with orthodontic corrections and decreasing of oral injuries by orthodontic wires.

BACKGROUND OF THE INVENTION

One of the most exercised orthodontic techniques is the so-called "sliding mechanics" according to which different types of brackets and appliances are attached in appropriate positions onto teeth and at least on both end molar teeth of a treated jaw which serve as anchors, with an arch-shaped wire (hereinafter in the description and claims to be referred to as an "arch wire"), held in a suitable groove within each of said brackets and retained thereto by a ligature member. Accordingly, all tooth movements such as straightening, leveling, rotating and arch forming of the teeth is obtained subject to the stresses applied thereon by the arch wire.

The last orthodontic appliance attached to a molar tooth on each side of a jaw is a tubular element which slidingly accommodates an end of the arch wire.

After the arch wire is placed within the brackets and fastened thereto by a ligature member such as a rubber band or a ligature wire or other means as known per se, the excessive length of the arch wire projecting at the rear of the tube is cut by a suitable cutter, leaving a protruding bit of 0.5 to 1.5 mm long.

When the dislocated teeth begin moving towards their correct position, the length of the arch wire between the tubes changes and may shorten as a result of which the protruding portion behind the tube appliances increases. Such an increase depends on the rate of movement of the dislocated teeth and also on the amount of force applied by external means, e.g. tensioned rubber bands and the patient's physiological response of bone to such force.

A significant character which should be kept throughout an orthodontic treatment is the arch shape of the arch wire which is a super-elastic metal or a shape memory metal which should be kept symmetrically about the axis of symmetry of the treated jaw. Failing to keep the arch wire in such symmetry will eventually yield to an asymmetric dental arch of the treated jaw.

However, the use of tubed appliances with the sliding mechanics technique involves some serious drawbacks concerning both the speed and effectiveness of an orthodontic treatment as well as the comfort and the possible oral injury of the patient.

One problem occurs when the arch wire slides out of its symmetric position with respect to that of the treated jaw, in which case the arch wire will eventually bring about an asymmetric arch forming of the set of teeth under treatment. Such sliding of an arch wire may occur, for example, due to a patient having bad chewing habits or chewing sticky foods, or due to other oral habits torsion, rubber bands or any other interfering mechanism. In this case, the arch wire protrudes more behind one tube and withdraws forward at the other. In extreme cases, the wire may even completely slide out of the tube at one side, and have a large distal projection behind the other tube.

Not only is the orthodontic treatment interfered by the dislocation of the arch wire, but also, the elongate arch wire's bit protruding excessively on one side may injure the patient's buccal-mucosa or gingiva.

Such problems occur in particular when long protruding bits (approximately 3 mm long or more) are intentionally left at the outset of the orthodontic treatment in order to prevent sliding of the arch wire out of the tubes, which may occur particularly when the arch wire is attached only to part of the teeth (either due to missing teeth or since primary teeth are not treated or for other orthodontic reasons), whereby, when chewing, the non-fixed portions of the wire are depressed or pulled resulting in the sliding of the wire out of one of the tubes and increasing its projection on the other side.

Heretofore, the problems arising from a sliding arch wire were addressed by bending the arch wire at portions extending from either end of the bracket to restrict the travel of the arch wire. As a result, replacement of the arch wire was required for each subsequent adjustment. This method is of course expensive and requires much time to adjust the wire, wasting valuable chairside time for the operator.

The buccal tube appliance mounted on a last molar tooth having a fixed orthodontic appliance also serves the purpose of generating a moment on the wire so as to apply a larger force on the dislocated teeth. If, however, the arch wire is only partially accommodated within the tube, thus, such moments are ineffective, or do not exist at all if the wire slides out of the tube.

It is the object of the present invention to provide an improved orthodontic buccal tube appliance for improving and shortening an orthodontic treatment as well as for preventing oral injury of a patient's mouth.

SUMMARY OF THE INVENTION

The present invention provides an orthodontic buccal tube device adapted to cooperate with an arch wire and comprising a base member for attachment to a tooth, and a body member which is fixed to said base member and which comprises a bore adapted to accommodate an end portion of the arch wire; said device being characterized in that it comprises an auxiliary member fixed to or integral with either said base member or said body member and being adapted for cooperation with an end of the wire protruding from said bore to either limit the rearward movement of the wire, or exert a force bringing to the development of a moment in the wire, or both.

The invention further provides an orthodontic buccal tube device adapted to cooperate with an arch wire and comprising a base member for attachment to a tooth, and a body member which is fixed to said base member and which comprises a bore adapted to accommodate an end portion of the arch wire; said device being characterized in that it comprises an auxiliary member fixed to or integral with either said base member or said body member and forming an abutment in the direction of the buccal-mucosa, thereby ensuring appropriate distance between the buccal-mucosa and the end of the wire so as to avoid injuries to said mucosa.

DESCRIPTION OF THE DRAWINGS

For better understanding, the present invention will now be described by way of example only and in a non-limiting manner, with reference to the accompanying drawings in which.

DESCRIPTION OF SPECIFIC EMBODIMENTS

Figure 1:
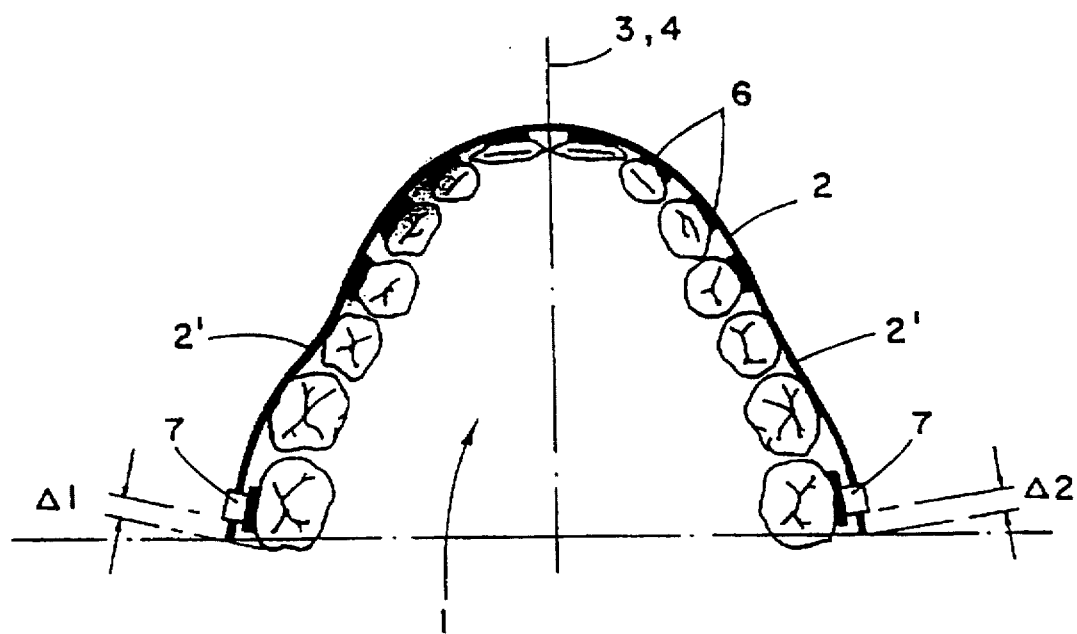
FIG. 1 is a schematic plan view of a set of teeth under a "sliding mechanics" orthodontic treatment, with the arch wire in its correct, symmetric position.

Reference is first made to FIG. 1 of the drawings which is a plan view of a set of teeth 1 under a "sliding mechanics" orthodontic treatment, using an arch wire 2 which is a super-elastic metal or a shape memory metal, preformed in an arch shape and has a line of symmetry 3 coinciding with the line of symmetry 4 of the set of teeth 1.

As known per se in the sliding mechanics orthodontic treatment, all the appliances attached to the teeth, except for the last one on each side of the mouth are brackets 6, while the last one on each side is a tubular appliances 7. The ends of the wire protrude at the rear of each tube 7, having lengths $\Delta_1$ and $\Delta_2$ essentially equal to one another, which lengths are determined by the tool used for dipping the wire such as a special 90° nose cutter where the lengths $\Delta_1$ and $\Delta_2$ are usually in the range of 0.5 to 1.5 mm long.

Figure 2:
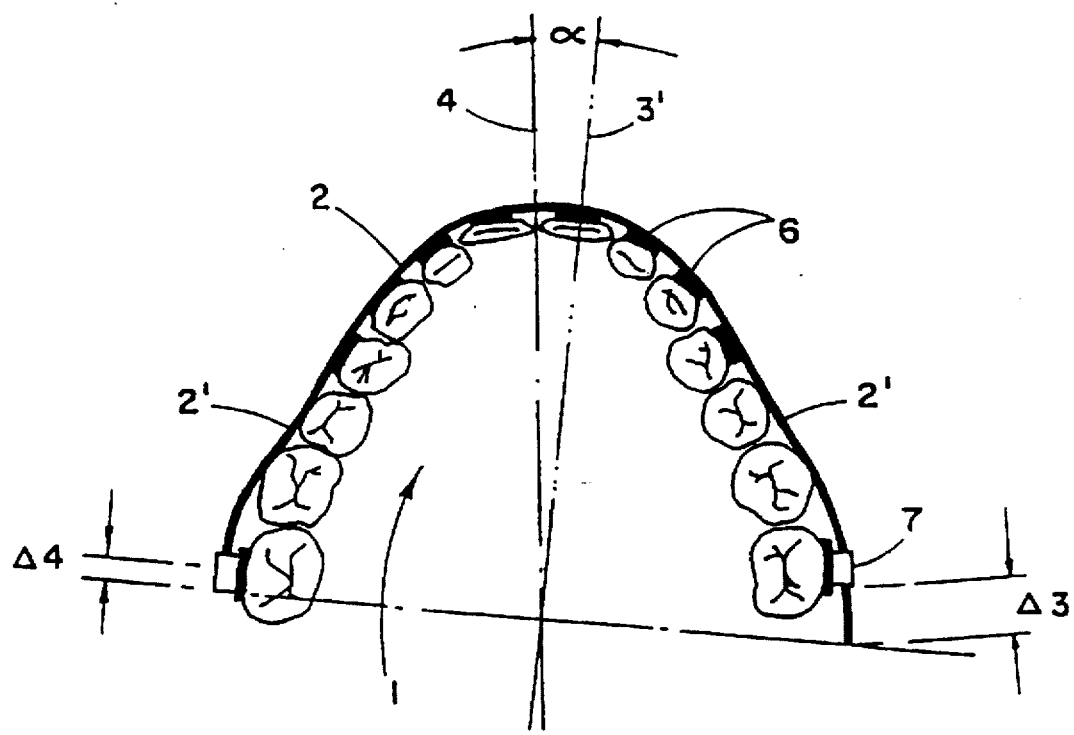
FIG. 2 is a schematic plan view as in FIG. 1 with the arch wire out of position.

However, some dislocations of the arch wire 2 may occur, for example, as illustrated in FIG. 2 in which the line of symmetry 3' of the arch wire 2 does not coincide with the line of symmetry 4 of the set of teeth 1, forming therebetween an angular displacement α and causing the arch wire 2 to protrude more at one side indicated $\Delta_3$ but on the other side the size of $\Delta_4$ decreases and may even reach a state at which the end of the wire slides out of the tube 7 altogether.

As already explained, in some cases the arch wire is attached only to the incisors and to part of the molar teeth, but in any case, the tubular appliance is attached to a last molar tooth on each side as seen in FIGS. 1 and 2. According to such an arrangement, essential long portions of the arch wire, indicated 2' remain unattached to teeth, resulting in a high risk of the wire sliding out of the tubes 7 due to incorrect chewing of food, or chewing of sticky food, e.g. chewing gum, etc, which will pull the wire out of the tube.

Figure 3:
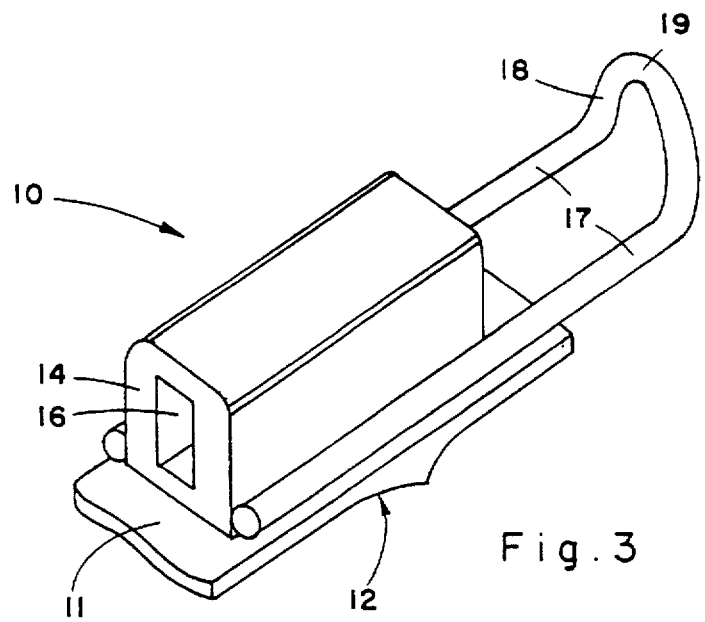
FIG. 3 is a perspective view of a buccal tube appliance according to one embodiment of the present invention.
Figure 4:
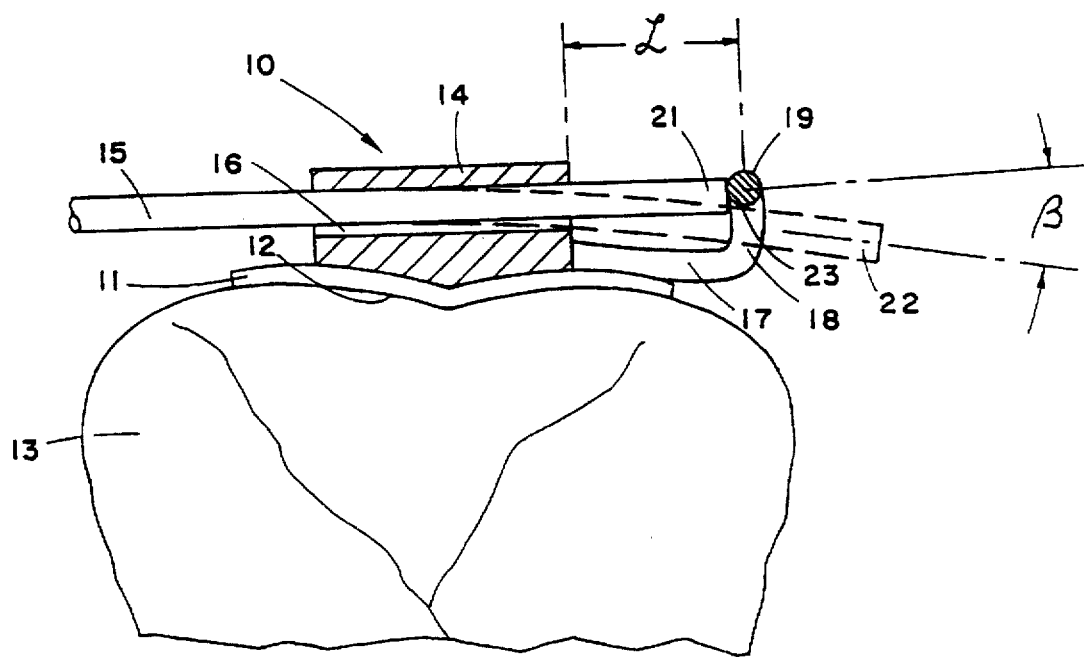
FIG. 4 is an enlarged, partially cut out top elevation, illustrating a molar moth with an appliance according to the present invention in cooperation with a portion of an arch wire.

Reference is now directed to FIGS. 3 and 4 of the drawings showing an orthodontic buccal tube appliance according to one embodiment of the present invention.

In the figures a buccal tube appliance generally designated 10 is constructed of a base pad 11 having a bottom surface 12 adapted for bonding directly on the buccal surface of a molar tooth 13 (seen only in FIG. 4) or alternatively attached to a molar band; A body member 14 has a longitudinal bore 16 of a rectangular cross-section suitable for slidably accommodating an arch wire 15 (seen in FIG. 4 having a circular cross-section).

Legs 17 of auxiliary member 18 having a U-shape, are attached to the body member 14 and alternatively to the base pad 11. As seen in FIG. 4, the auxiliary member 18 is assembled at the rear of the tube and its construction is such that its apex 19 is aligned with the center line of the bore 16 so as to establish an obstacle for an end 21 of the arch wire 15, whereby, the latter is prevented from further distal regression as illustrated in FIG. 4 by the full line.

However, whenever required, the orthodontist may enable further distal regression of the arch wire by deflecting its end 22 as shown in FIG. 4 and indicated by dashed lines. According to such an arrangement, a bending moment is applied on the arch wire 15, the magnitude of said moment depending both on the angle β formed between the center line of bore 16 and the actual longitudinal axis of the diverted wire 22 and on the distance L defined between the rear end of the tube and the point of contact 23 of the deflected arch wire 22 with the member 18.

By applying a suitable moment, larger forces are applied on the dislocated teeth, thus an increased relocation of teeth may be obtained with a controlled elongation of the protruding portion 22 of the deflected arch wire, which requires increased force for small advance of the wire protruding, eliminating oral injury due to diversion of the arch wire's end.

If required, the apex of the auxiliary member may be slightly shifted in the buccal direction where it is no longer in alignment with the center line of the bore, whereby, when the arch wire reaches the apex it may continue its distal regression by self deflection. The advantage of this embodiment is that it does not require the interference of the orthodontist.

Further attention is now made to FIGS. 5 to 11, illustrating further embodiments only of the auxiliary member 18 for use with an appliance in accordance with the present invention. However, it should be obvious to a person versed in the art that many other forms of the auxiliary member 18. may be used for either or both limiting the advancement of the arch wire or diverting it and possibly applying a moment thereon.

Figure 6:
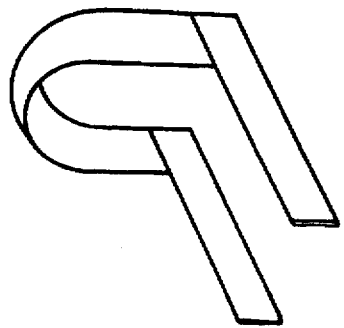
Figure 7:
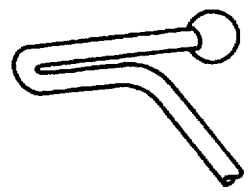
Figure 5:
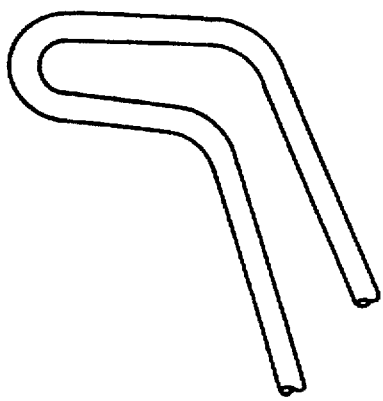

FIG. 5 illustrates a basic form of a head portion being a wire bent into a U-shape with two legs integral with the arms of the U-shaped head portion. FIG. 6 is of the same shape but is made of a flat strap rather than bent wire. FIG. 7 shows a U-shaped head portion with a single leg attached to one arm of the U-shaped head portion, and a bulge at the free arm of the head portion, to prevent injury of the buccal-mucosa.

Figure 8:
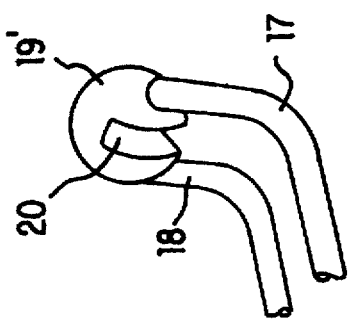

Special attention is directed to FIG. 8 in which the auxiliary member 18 consists of legs 17 for attachment to the appliance and a spherical head member 19' provided with a slot 20 having right angled walls. According to such a construction torsion moments can be applied on to a rectangular cross-sectioned arch wire, by changing the angular position at member 19' with respect to the bore of the device.

Figure 10:
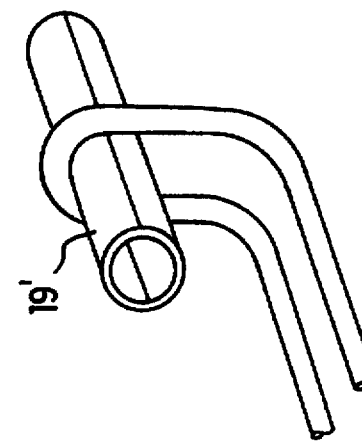
Figure 9:
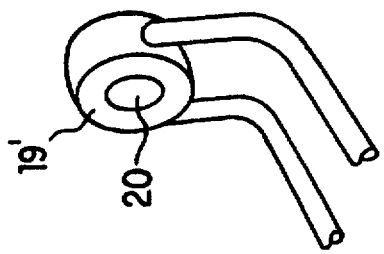

Similar effects may be obtained by the embodiments of FIGS. 9 and 10 which are useful for exercising bending moments on the arch wire by simply changing the angular position of the end member 19' which in FIG. 9 is a bored spherical segment and in FIG. 10 is a tube attached to a U-shaped head portion.

Figure 11:
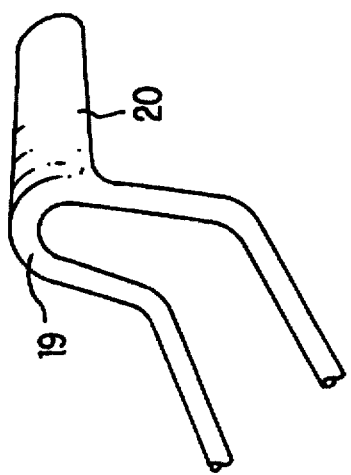
FIGS. 5 to 11 are perspective views of different auxiliary members of a buccal tube appliance according to the present invention.

In FIG. 11, the head member 19' comprises a guard member 20 useful in guarding and protecting the buccal-mucosa from injury by an end of the arch wire.

FIGS. 12 to 17 of the drawings illustrate different embodiments of buccal tube appliances according to the present invention.

Figure 12:
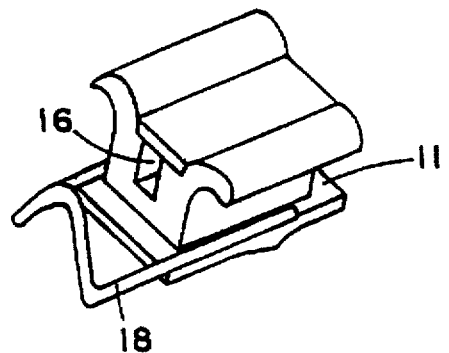
FIGS. 12 to 17 are perspective views of different embodiments of the present invention.

FIG. 12 is a buccal tube appliance having a rectangular cross-sectioned bore 16 with the auxiliary member 18 attached to the base pad 11.

Figure 13:
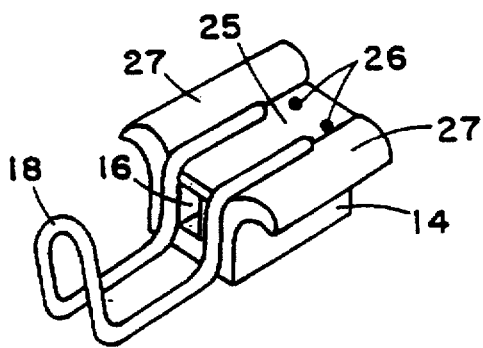

FIG. 13 illustrates a buccal appliance having a convertible cover 25 which is attached provisionally by point weldings 26 to the body member 14, which body member further comprises bracket wings 27. The arrangement is such that upon removal of the convertible cover 25, the tube appliance is converted into an orthodontic bracket with the bracket wings 27 serving for cooperation with a ligature wire or other arch wire retaining means as known per se such as rubber bands.

Furthermore, according to the embodiment of FIG. 13, the member 18 is attached to the convertible cover 25 whereby when the appliance is no more required as a tubular appliance, it may be used as a bracket and the member 18 is removed with the cover 25.

Figure 14:
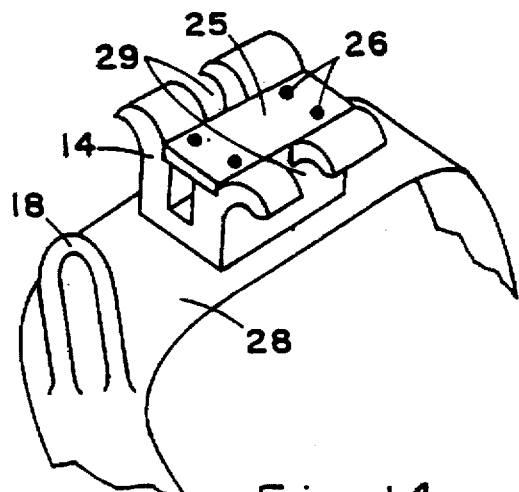

FIG. 14 illustrates an appliance in accordance with the present invention also having a convertible cover 25 provisionally attached by point weldings 26 and whereby the body member 14 as well as the auxiliary member 18 are attached directly to a molar band 28 embracing a molar tooth. Furthermore, according to this embodiment, the wings 27 are split by grooves 29 so as to facilitate attaching an arch wire thereto for rotation control.

Figure 15:
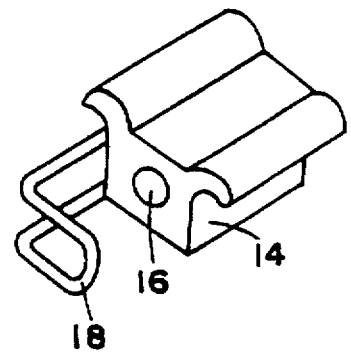
Figure 16:
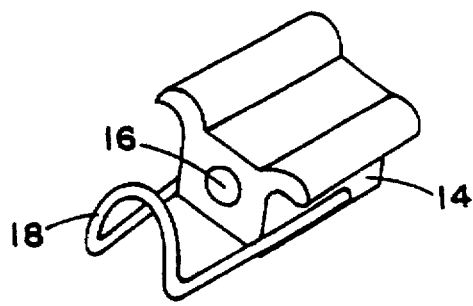

In the embodiment of FIGS. 15 and 16 the bores 16 are of cylindrical cross-sections and the auxiliary members 18 are attached at different locations to the body member 14.

Figure 17:
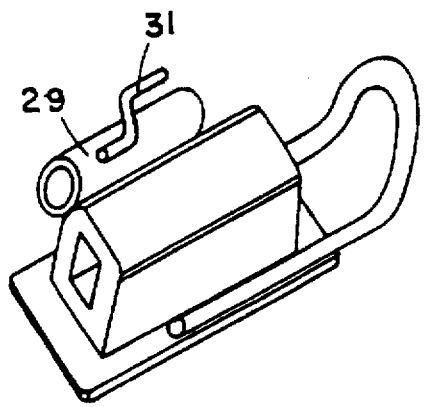

FIG. 17 of the drawings illustrates a further embodiment in accordance with the present invention further comprising a tubular member 29 for cooperation with a face bow of a head gear or with a lip bumper. Furthermore, a hook 31 is attached to the tube 29 which hook is used for facilitating movement of the teeth in a desired direction by fastening rubber bands between hooks attached to other teeth either on the same jaw or on the other jaw.

It is readily understood that the teachings of the present invention are applicable mutatis mutandis to a large variety of orthodontic buccal appliances as explained above.

We claim:

1. An orthodontic buccal tube device for use with a plurality of teeth, comprising:
   an arch wire having an end face transverse to a longitudinal axis of the arch wire and a surface parallel to the axis;
   a base member for attaching the device to one of said plurality of teeth;
   a body member attached to the base member and having a bore with a rectangular cross-section, the bore having an entry side and an exit side and being configured to receive the arch wire; and
   an auxiliary member projecting from one end of the body member adjacent the exit side of the bore, the auxiliary member having an abutment portion axially aligned with the bore and a deflection portion offset from the abutment portion in a direction towards the base member, the auxiliary member being engageable with the arch wire by one of:
   (i) abutment between the end face of the arch wire and the abutment portion to prevent axial movement of the arch wire beyond the abutment portion; and
   (ii) engagement between the deflection portion and the surface of the arch wire, thereby developing a moment therein through a force applied to the arch wire by the deflection portion.

2. A device according to claim 1, wherein said auxiliary member is attached to said base member.

3. a device according to claim 1, wherein said auxiliary member is attached to said body member.

4. A device according to claim 1, wherein said auxiliary member has a leg portion and a head portion, the leg portion being attached to one of said base member and said body member and defining a first plane, and the head portion defining a second plane, said first and said second planes being at an angle with respect to each other and said head portion being adapted for said cooperation with the arch wire.

5. A device according to claim 4, wherein said first and said second planes are essentially normal to each other.

6. A device according to claim 4, wherein said auxiliary member has a U-shaped head portion.

7. A device according to claim 6, wherein the leg portion of the auxiliary member includes a single member connected to an arm of the U-shaped head portion in said second plane.

8. A device according to claim 6, wherein said leg portion comprises two essentially parallel members, each of said parallel members being connected to one of the arms of the U-shaped head portion.

9. A device according to claim 6, wherein the deflection portion includes an opening defined by an interior of the U-shaped head portion.

10. A device according to claim 4, wherein said head portion of the auxiliary member comprises a spherical segment having a central bore adapted to receive the end portion of the arch wire.

11. A device according to claim 10, wherein said central bore has an axis which extends at an angle to the bore in said body member.

12. A device according to claim 4, wherein said head portion of the auxiliary member comprises a tube adapted to receive the end portion of the arch wire.

13. A device according to claim 4, wherein said head member comprises a grooved member.

14. A device according to claim 4, wherein the deflection portion includes an opening at least partially defined by the leg portion and the head portion.

15. A device according to claim 1, wherein the deflection portion includes an inner surface of the stop portion.

16. A device according to claim 1, wherein the auxiliary member is detachable from the body member.

17. An orthodontic buccal tube device for use with a plurality of teeth and configured to engage an arch wire having an end face transverse to a longitudinal axis of the arch wire and a surface parallel to the axis, the device comprising:
   a base member for attaching the device to one of said plurality of teeth;
   a body member attached to the base member and having a bore with a rectangular cross-section, the bore having an entry side and an exit side and being configured to receive the arch wire; and
   an auxiliary member projecting from one end of the body member adjacent the exit side of the bore, the auxiliary member having an abutment portion axially aligned with the bore and a deflection portion offset from the abutment portion in a direction towards the base member, said auxiliary member also having a leg portion and a head portion, the leg portion being attached to one of said base member and said body member and defining a first plane, and the head portion defining a second plane, said first and said second planes being at an angle with respect to each other and said head portion being adapted for cooperation with the arch wire, said head portion also includes a spherical segment having a central bore adapted to receive the end portion of the wire, wherein the auxiliary member is engageable with the arch wire by one of:

(i) abutment between the end face of the arch wire and the abutment portion to prevent axial movement of the arch wire beyond the abutment portion; and (ii) engagement between the deflection portion and the surface of the arch wire, thereby developing a moment therein through a force applied to the arch wire by the deflection portion.

18. A device according to claim 17, wherein the central bore has an axis that extends at an angle to the bore of the body-member.

19. A device according to claim 17, wherein the auxiliary member is detachable from the body member.

* * * * *